(12) United States Patent
Ji et al.

(10) Patent No.: US 11,505,580 B2
(45) Date of Patent: Nov. 22, 2022

(54) LEECH POLYPEPTIDE AND USE THEREOF

(71) Applicant: SHANDONG UNIVERSITY, Shandong (CN)

(72) Inventors: Aiguo Ji, Weihai (CN); Shuliang Song, Weihai (CN)

(73) Assignee: SHANDONG UNIVERSITY, Shandong (CN)

( * ) Notice: Subject to any disclaimer, the term of this patent is extended or adjusted under 35 U.S.C. 154(b) by 225 days.

(21) Appl. No.: 16/770,026

(22) PCT Filed: Sep. 24, 2019

(86) PCT No.: PCT/CN2019/107585
§ 371 (c)(1),
(2) Date: Jun. 4, 2020

(87) PCT Pub. No.: WO2020/228218
PCT Pub. Date: Nov. 19, 2020

(65) Prior Publication Data
US 2022/0162273 A1    May 26, 2022

(30) Foreign Application Priority Data

May 13, 2019   (CN) .......................... 2019103941086

(51) Int. Cl.
| | | |
|---|---|---|
| *C07K 7/08* | (2006.01) | |
| *A61K 38/10* | (2006.01) | |
| *A61K 38/00* | (2006.01) | |
| *C07K 14/435* | (2006.01) | |

(52) U.S. Cl.
CPC .......... *C07K 14/43536* (2013.01); *C07K 7/08* (2013.01); *A61K 38/00* (2013.01)

(58) Field of Classification Search
CPC .... C07K 7/08; C07K 14/43536; A61K 38/10; A61K 38/00
See application file for complete search history.

(56) References Cited

FOREIGN PATENT DOCUMENTS

| | | |
|---|---|---|
| CN | 101514231 A | 8/2009 |
| CN | 107287269 A | 10/2017 |
| CN | 110066318 A | 7/2019 |

OTHER PUBLICATIONS

Hu et al., "A peptide inhibitor of macrophage migration in atherosclerosis purified from the leech *Whitmania pigra*," Journal of Ethnopharmacology, 2020, 254: 1-13. (Year: 2020).*
Li, Ying, "Study on Isolation, Purification and Mechanism of Hirudin Peptide with Activity of Inhibiting Macrophage Migration," Thesis for Master Degree, Shandong University, May 14, 2017.
Feb. 18, 2020 International Search Report issued in International Patent Application No. PCT/CN2019/107585.
Feb. 18, 2020 Written Opinion of the International Searching Authority issued in International Patent Application No. PCT/CN2019/107585.

* cited by examiner

*Primary Examiner* — Julie Ha
(74) *Attorney, Agent, or Firm* — Oliff PLC (57) ABSTRACT

A leech polypeptide with activity to inhibit macrophage migration in vitro, which is useful in the prevention of atherosclerosis. The preparation method of the leech peptide includes: firstly, a leech zymolyte HE is prepared from Whitmania *pigra* Whitman, and the amino acid sequence of leech polypeptide HE 4-1 is obtained and synthesized artificially after analysis and sequencing.

6 Claims, 12 Drawing Sheets
Specification includes a Sequence Listing.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
```

```
<223> OTHER INFORMATION: Synthetic Construct

<400> SEQUENCE: 1

Glu Ala Gly Ser Ala Lys Glu Leu Glu Gly Asp Pro Val Ala Gly
1               5                   10                  15
```

LEECH POLYPEPTIDE AND USE THEREOF

The present application contains a Sequence Listing that has been submitted electronically in ASCII format and is hereby incorporated by reference in its entirety. The ASCII copy, created on Oct. 26, 2021, is named Substitute Sequence Listing_ST25.txt and is 560 bytes in size.

FIELD OF THE INVENTION

The present invention relates to the field of biopharmaceutical technology, and particularly to a leech polypeptide and use thereof.

BACKGROUND OF THE INVENTION

Information disclosed in the background section is merely for the purpose of facilitating the understanding of the general background of the present invention and is not necessarily to be taken as an acknowledgment or any form of suggestion that the information constitutes prior art that is already known to those of ordinary skill in the art.

Cardio-cerebrovascular diseases is a worldwide disease with the highest morbidity, mortality and disability, which seriously threatens the survival and quality of human life. According to the data from WHO, approximately 17.5 million people worldwide die of cardiovascular disease each year. The "2018 Report on Cardiovascular Diseases in China" issued by the National Center for Cardiovascular Diseases states that there are approximately 290 million patients with cardiovascular diseases in China. Cardiovascular diseases contribute to more than 40% of the deaths with diseases, are the leading cause of death in China, and have become a major public health problem in China. Atherosclerosis (AS) is a fundamental pathological basis for the occurrence and development of cardiovascular and cerebrovascular diseases. The development of AS can go through decades, and the cardiovascular diseases thus caused have generally entered the late stage when symptoms appear. In fact, the formation of fatty streaks in the early stage of AS can be seen in childhood. Although no clinical symptoms are caused, it can be proved that the development of the disease is a slow and long-term process, so the early prevention and treatment of AS has become particularly important.

As a chronic disease, AS has a complicated etiology, and decades of laboratory and clinical research have provided a preliminary insight into the pathological process of AS. The theory of "inflammation-injury-response" proposed by Russell Ross in 1980 is widely supported and accepted, which is complementary to the "lipid infiltration theory" and explains the whole process of the occurrence and development of AS more completely. At present, it is believed that in the early stage of AS, a variety of risk factors, such as hyperlipidemia, hypertension, hyperglycemia, and smoking, cause damage to vascular endothelial cells and monocytes, thereby causing a large number of cell adhesion molecules to be expressed on the surface of both cells. E-selectin and P-selectin on vascular endothelial cells and L-selectin on monocytes bind their ligands, which mediates the initial rolling adhesion of monocytes on vascular endothelial cells. Vascular endothelial cells release chemokines such as monocyte chemoattractant protein-1 (MCP-1), causing vascular cell adherent molecule-1 (VCAM-1) and intercellular adherent molecule-1 (ICAM-1) on the cell membrane to be activated and bind to integrins on the surface of leukocytes, such as very late antigen-4 (VLA-4) and lymphocyte function associated antigen-1 (LFA-1) to trigger firm adhesion. Once firm adhesion occurs, the monocytes migrate across the vascular endothelium into the lining of the vascular intima. The monocytes infiltrating the intima are differentiated into macrophages under the action of macrophage colony stimulating factor (MCSF). Macrophages engulf lipids in large quantities through scavenger receptors, such as CD36, and then transform into macrophage-derived foam cells. Moreover, the macrophages also release chemokines, which induce the migration of medial smooth muscle cells into the intima. The latter can also engulf lipids and transform into smooth muscle cell-derived foam cells. Foam cells are accumulated in the intima and form fatty streak in the early lesion of AS. As AS continues to develop, T cells express IFN-γ and CD40 to activate macrophages. The activated macrophages further secrete cytokines and growth factors to promote the migration and proliferation of smooth muscle cells. The latter synthesizes and secretes a large amount of collagen fibers, covering the surface of the plaque to form the fibrous plaque phase of AS. With the persistence of inflammation, the macrophages release matrix metalloproteinases (MMP) to degrade the collagen, and NO as well to induce the apoptosis of foam cells, thereby promoting AS to progress to the atherosclerotic plaque phase. Due to the instability of atherosclerotic plaques, many secondary lesions can be easily caused, such as thrombosis, plaque rupture, intraplaque hemorrhage, and aneurysm, etc., leading to the occurrence of severe cardiovascular diseases such as myocardial infarction, cerebral hemorrhage, and cerebral infarction. Therefore, monocytes/macrophages are not only immune cells that enter the AS site initially, but also play a key role in the formation, development, and outcome of AS plaques.

The occurrence of AS is the result of the combined effects of multiple factors. At present, there are many risk factors for AS that have been found. However, the existing targeted treatments and control results are both not satisfactory. Lipid-lowering and anti-inflammatory treatments are currently the most important treatment measures. More and more evidences show that immune responses (firstly, the immune response of macrophages) are involved in all aspects of AS development. Compared with normal mice, immunodeficiency mice have about 70% less severe AS and unchanged serum cholesterol level. Therefore, the mechanism of inflammation and immune regulation has become a hot spot in AS research at present, and the research on this mechanism will open a new path for the treatment of AS. However, too many adverse reactions will occur if the immune system is completely suppressed. From the process of occurrence and development of AS, it can be found that monocytes/macrophages are the primary cells of the immune system participating in AS; and the regression of AS plaques are also accompanied by a decrease in macrophages in the plaques, and conversely, the progression of AS plaques is accompanied by an increase in macrophages. Therefore, if the migration of macrophages to the AS site is able to be inhibited, it is possible to delay the development of AS with a small impact on the immune system, which is of important practical significance for preventing the occurrence of AS.

Whitmania *pigra* Whitman, as one of the traditional Chinese medicines commonly used in clinical practice, has been found in ancient medical books for use in the treatment of many diseases. It is mentioned in Shen Nong's Materia Medica to mainly function to remove bad blood and blood stasis, treat menopause, disperse the blood stasis and dissipate accumulation". Whitmania *pigra* Whitman has a wide range of pharmacological effects, including anticoagulation, anti-thrombotic, anti-tumor, anti-inflammatory, and anti-fibrotic effects. In recent years, the research on Whitmania *pigra* Whitman in cardiovascular and cerebrovascular diseases has been continuously deepened, and Whitmania *pigra* Whitman has found more and more use in cardiovascular and cerebrovascular diseases. Clinically, Whitmania *pigra* Whitman has been widely used in the treatment of coronary heart disease, angina pectoris, acute myocardial infarction, ischemic stroke, cerebral hemorrhage, atherosclerosis and peripheral vascular disease. Except for hirudin and derivative preparations thereof that have thrombin inhibitory effect, most of the other preparations are produced with Whitmania *pigra* Whitman as a whole, without systematic separation and purification. Whitmania *pigra* Whitman as a traditional Chinese medicine is widely used in clinical practice. However, the present inventors have found that due to the complex composition in Whitmania *pigra* Whitman, it is difficult to control the quality of medicinal materials, and there are many adverse reactions. The most severe adverse reaction is bleeding, so regular monitoring of blood clotting is needed for patients who have been taking Whitmania *pigra* Whitman preparations for a long time.

SUMMARY

Based on the above-mentioned shortcomings of the prior art, the present invention provides a leech polypeptide with activity to inhibit macrophage migration in vitro, which is useful in the prevention of atherosclerosis. In the present invention, a leech zymolyte HE is firstly prepared from Whitmania *pigra* Whitman. After further analysis and sequencing, the amino acid sequence of leech polypeptide HE 4-1 is finally obtained and artificially synthesized. As verified by experiments, the artificially synthesized leech polypeptide also has the activity to inhibit macrophage migration, and is therefore of great value for practical use.

According to a first aspect of the present invention, a leech polypeptide is provided. The amino acid sequence of the leech polypeptide is EAGSAKELEGDPVAG (SEQ ID NO: 1). The leech polypeptide has the effect of inhibiting the migration activity of macrophages, and can be synthesized by solid-phase polypeptide synthesis.

According to a second aspect of the present invention, a leech polypeptide fragment is provided, which has a main amino acid sequence that is ≥70% identical and ≥90% similar to the main amino acid sequence of above-mentioned leech polypeptide, and is a leech polypeptide comprising 3 or 4 or 5 amino acids truncated from any position of the 15-amino-acid sequence and having the same biological activity as the leech polypeptide.

According to a third aspect of the present invention, a leech polypeptide analogue inhibiting macrophage migration is provided, which has the same biological activity as the leech polypeptide. The leech polypeptide analogue is a biologically active polypeptide sequence or protein formed by fusing the leech polypeptide to another compound or fusing the amino acid sequence of the leech polypeptide to another polypeptide or protein.

According to a fourth aspect of the present invention, a leech polypeptide derivative inhibiting macrophage migration is provided, which has an amino acid sequence that is ≥70% identical and ≥90% similar to the main amino acid sequence of the leech polypeptide. The derivative is a leech polypeptide obtained by substituting a group of one or more amino acids in the amino acid sequence with an additional group and having the same biological activity as the leech polypeptide.

According to a fifth aspect of the present invention, a leech polypeptide variant inhibiting macrophage migration is provided, which has an amino acid sequence that is ≥70% identical and ≥90% similar to the main amino acid sequence of the leech polypeptide. The variant is an amino acid sequence or an encoding nucleotide sequence thereof having one or several amino acid or nucleotide changes including deletion, insertion or replacement of amino acid(s) or nucleotide(s) at any position(s) in the amino acid sequence or nucleotide sequence, or addition of amino acid(s) or nucleotide(s) at two ends of the sequence.

According to a sixth aspect of the present invention, a nucleotide encoding the leech polypeptide, the leech polypeptide fragment, the leech polypeptide analogue, the leech polypeptide derivative, or the leech polypeptide variant is provided, which comprises any one of:

(a) a nucleotide encoding a polypeptide having the amino acid sequence or a fragment, an analogue, a derivative or a variant thereof;

(b) a nucleotide complementary to the nucleotide in (a); and (c) a nucleotide that is ≥75% identical to the nucleotide in (a) or (b).

The nucleotide is produced by artificial synthesis.

According to a seventh aspect of the present invention, use of the leech polypeptide, the leech polypeptide fragment, the leech polypeptide analogue, the leech polypeptide derivative, and the leech polypeptide variant in the preparation of drugs for preventing or treating related diseases caused by macrophage migration, and diagnosing and detecting the occurrence and severity of these related diseases.

Preferably, the disease includes atherosclerosis.

The present invention has the following beneficial effects.

In the present invention, a leech zymolyte HE is prepared from Whitmania *pigra* Whitman. After further analysis and sequencing, the amino acid sequence of leech polypeptide HE 4-1 is finally obtained and artificially synthesized. As verified by experiments, the artificially synthesized leech polypeptide also has the activity to inhibit macrophage migration. Therefore, it has potential value for preventing and/or treating atherosclerosis and related diseases, and has a good prospect for practical application.

BRIEF DESCRIPTION OF THE DRAWINGS

The accompanying drawings constituting a part of the present invention are used for providing further understanding for the present invention. Exemplary embodiments of the present invention and descriptions thereof are used for explaining the present invention and do not constitute an improper limitation to the present invention.

FIG. 2 shows the effect of HE1-HE6 on the migration activity of macrophages RAW264.7 in Example 1 of the present invention, in which FIG. 2(A) shows the migration result of macrophages RAW264.7 (100×); and FIG. 2(B) shows the statistical result of cell count in the lower chamber. **$p<0.01$ VS controlgroup, #$p<0.05$ VS LPS group, and ##$p<0.01$ VS LPS group.

FIG. 4(A) shows the migration result of macrophages RAW264.7 after treatment with HE4-1 (100×); FIG. 4(B) shows the statistical result of cell count in the lower chamber after treatment with HE4-1; FIG. 4(C) shows the migration result of macrophages RAW264.7 after treatment with HE4-2 (100×); and FIG. 4(D) shows the statistical result of cell count in the lower chamber after treatment with HE4-2. *$p<0.05$ VS control group, **$p<0.01$ VS control group, #$p<0.05$ VS LPS group.

FIG. 7 shows the effect of HE4-1 on the migration activity of macrophages RAW264.7 in Example 1 of the present invention, in which FIG. 7(A) shows the migration result of macrophages RAW264.7 (100×); and FIG. 7(B) shows the statistical result of cell count in the lower chamber. **$p<0.01$ VS control group, #$p<0.05$ VS LPS group.

FIG. 10 shows the effect of HE-D on the migration activity of macrophages RAW264.7 in Example 4 of the present invention, in which FIG. 10(A) is a photograph showing the effect of HE-D on the migration activity of macrophages RAW264.7 based on Transwell assay; and FIG. 10(B) is a histogram of statistical data.

FIG. 11 shows the effect of HE-D on JNK and p38 signaling pathways in RAW264.7 cells induced with LPS in Example 5 of the present invention, in which FIG. 11(A) shows the result of Western blot of JNK and p38 signaling pathways; and FIG. 11(B) shows the result of data processing by Image J. *$p<0.05$ VS LPS group.

FIG. 12 shows the effect of HE-D on the phagocytosis ability and lysozyme secretion ability of RAW264.7 cells in Example 6 of the present invention, in which FIG. 12(A) shows that HE-D has no significant effect on the phagocytosis ability of macrophages; and 12(B) shows that HE-D has no significant effect on the lysozyme secretion ability of macrophages. ***$p<0.001$ VS control group.

FIG. 13 shows the effect of HE-D on the secretion of IL-1, IL-6, IL-12, and TNF-α by RAW264.7 cells in Example 6 of the present invention, in which FIG. 13(A) shows that HE-D has no significant effect on IL-1 secretion by macrophages; FIG. 13(B) shows that HE-D has no significant effect on IL-6 secretion by macrophages; FIG. 13(C) shows that HE-D has no significant effect on IL-12 secretion by macrophages; and FIG. 13(D) shows that 400 and 800 μg/mL HE-D can promote the secretion of TNF-α. *$p<0.05$ VS control group, ***$p<0.001$ VS control group.

DETAILED DESCRIPTION

It should be noted that the following detailed description is exemplary and is intended to provide a further description of the present invention. Unless otherwise specified, all technical and scientific terms used in the present invention have the same meaning as commonly understood by those of ordinary skill in the art to which the present invention belongs.

It should be noted that terms used herein are only for describing specific implementations and are not intended to limit exemplary implementations according to the present invention. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

As described above, due to the complex composition in Whitmania pigra Whitman, it is difficult to control the quality of medicinal materials, and there are many adverse reactions. The most severe adverse reaction is bleeding, so regular monitoring of blood clotting is needed for patients who have been taking Whitmania pigra Whitman preparations for a long time.

In view of this, in a typical embodiment of the present invention, a leech polypeptide is provided. The main amino acid sequence of the leech polypeptide is EAGSAKELEGDPVAG (SEQ ID NO: 1). The leech polypeptide has the effect of inhibiting the migration of macrophages.

The synthesized leech polypeptide (designated as HE-D) in the present invention has a sequence abbreviated as EAGSAKELEGDPVAG (SEQ ID NO: 1), a molecular weight of 1429.294 Da, and a sequence of Glu-Ala-Gly-Ser-Ala-Lys-Glu-Leu-Glu-Gly-Asp-Pro-Val-Ala-Gly (SEQ ID NO: 1), where:

Glu represents glutamic acid, and is a residue of the amino acid glutamic acid;

Ala represents alanine, and is a residue of the amino acid alanine;

Gly represents glicine, and is a residue of the amino acid glicine;

Ser represents serine, and is a residue of the amino acid serine;

Lys represents lysine, and is a residue of the amino acid lysine;

Leu represents leucine, and is a residue of the amino acid leucine;

Asp represents aspartic acid, and is a residue of the amino acid aspartic acid;

Pro represents proline, and is a residue of the amino acid proline; and

Val represents valine, and is a residue of the amino acid valine.

The polypeptide of the present invention can be artificially synthesized by solid-phase polypeptide synthesis. Specifically, the amino acid sequence is obtained following a standard Fmoc protocol, screening by a resin, and a reasonable method for polypeptide synthesis. The C-terminal carboxyl group of the target polypeptide is covalently linked to an insoluble polymer resin, and then the amino group of this amino acid is used as a starting point to interact with the carboxyl group of another molecule of amino acid to form a peptide bond. This process is repeated continuously to obtain the target polypeptide product. After the synthesis reaction is completed, the protecting group is removed, and the polypeptide chain is separated from the resin to obtain the target product. Polypeptide synthesis is a process of repeatedly adding amino acids, and the solid-phase synthesis is synthesis from the C-terminus to the N-terminus.

It has been proved by experiments that the leech polypeptide HE-D provided in the present invention can exert an inhibitory effect on macrophage migration by regulating the levels of JNK and p38 phosphorylation. HE-D has basically no effect on the biological functions of macrophages at the same time of inhibiting the migration of macrophages, which can effectively reduce the adverse reactions caused by HE-D. Therefore, synthetic leech polypeptide HE-D can be used for the early prevention of atherosclerosis and has the potential to prevent the further development of AS.

In a further specific embodiment of the present invention, a leech polypeptide fragment is provided, which has a main amino acid sequence that is ≥70% identical and ≥90% similar to the main amino acid sequence of above-mentioned leech polypeptide, and is a leech polypeptide comprising 3 or 4 or 5 amino acids truncated from any position of the 15-amino-acid sequence and having the same biological activity as the leech polypeptide.

In a further specific embodiment of the present invention, a leech polypeptide analogue inhibiting macrophage migration is provided, which has the same biological activity as the leech polypeptide. The analogue is a biologically active polypeptide sequence or protein formed by fusing the leech polypeptide to another compound or fusing the amino acid sequence of the leech polypeptide to another polypeptide or protein.

In a further specific embodiment of the present invention, a leech polypeptide derivative inhibiting macrophage migration is provided, which has an amino acid sequence that is ≥70% identical and ≥90% similar to the main amino acid sequence of the leech polypeptide. The derivative is a leech polypeptide obtained by substituting a group of one or more amino acids in the amino acid sequence with an additional group and having the same biological activity as the leech polypeptide.

In a further specific embodiment of the present invention, a leech polypeptide variant inhibiting macrophage migration is provided, which has an amino acid sequence that is ≥70% identical and ≥90% similar to the main amino acid sequence of the leech polypeptide. The variant is an amino acid sequence or an encoding nucleotide sequence thereof having one or several amino acid or nucleotide changes including deletion, insertion or replacement of amino acid(s) or nucleotide(s) at any position(s) in the amino acid sequence or nucleotide sequence, or addition of amino acid(s) or nucleotide(s) at two ends of the sequence.

In a further specific embodiment of the present invention, a nucleotide encoding the leech polypeptide, the leech polypeptide fragment, the leech polypeptide analogue, the leech polypeptide derivative, or the leech polypeptide variant is provided, which comprises any one of:
(a) a nucleotide encoding a polypeptide having the amino acid sequence or a fragment, an analogue, a derivative or a variant thereof;
(b) a nucleotide complementary to the nucleotide in (a); and
(c) a nucleotide that is ≥75% identical to the nucleotide in (a) or (b).

The nucleotide is produced by an artificial synthesis.

In a further specific embodiment of the present invention, use of the leech polypeptide, the leech polypeptide fragment, the leech polypeptide analogue, the leech polypeptide derivative, and the leech polypeptide variant in the preparation of drugs for preventing or treating related diseases caused by macrophage migration such as atherosclerosis, and diagnosing and detecting the occurrence and severity of these related diseases. The disease includes atherosclerosis.

In a further specific embodiment of the present invention, the leech polypeptide is used for preparing a drug useful as a protease inhibitor, promoter or affinity reagent, or a detection reagent.

The present invention is further illustrated through examples below; however the present invention is not limited thereto. It is to be understood that these examples are merely illustrative of the present invention and are not intended to limit the scope of the present invention.

EXAMPLE 1

Separation and Purification of Leech Polypeptide

In this example, a leech zymolyte HE was firstly prepared from Whitmania *pigra* Whitman by enzymolysis. After establishing a model of LPS-induced macrophage RAW264.7 migration, Transwell migration assay showed that HE can inhibit the macrophage migration in a concentration-dependent manner. Then, HE was separated and purified by chromatography on QSepharose FF strong basic anion exchange column, and chromatography on Superdex30, Superdexpeptide and G10 gel column, and Transwell assay was done to track the activity. Finally leech polypeptide HE4-1 having activity to inhibit the migration of macrophages RAW264.7 was obtained.

Figure 1:
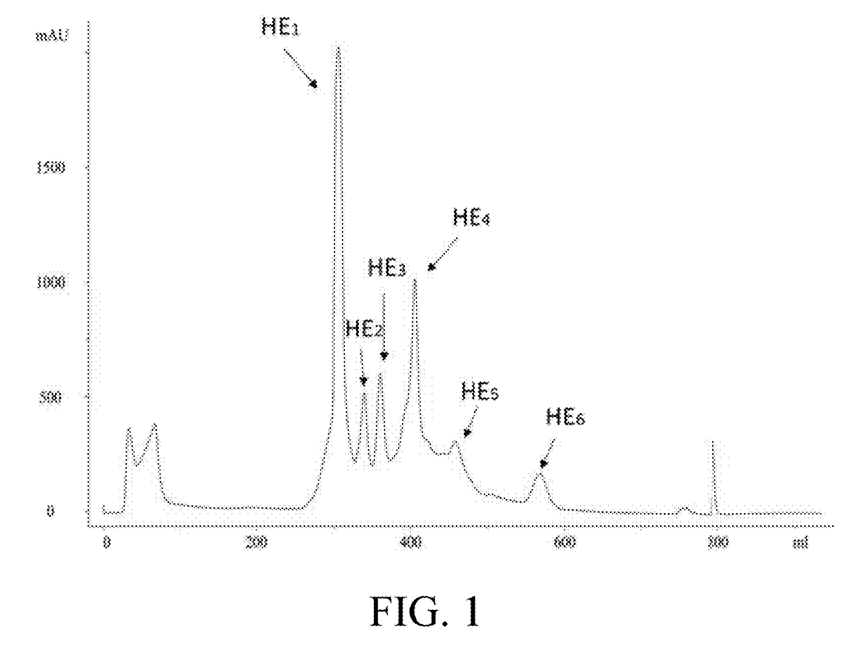
FIG. 1 shows an elution curve by chromatography on Q Sepharose FF strong basic anion column of HE in Example 1 of the present invention.

The QSepharoseFF strong basic anion column was used for the first separation of HE. As shown in FIG. 1, HE was separated into 6 peaks. The products of each eluted peak were collected, and lyophilized after alcohol precipitation and desalting to obtain HE1-HE6.

Figure 2:
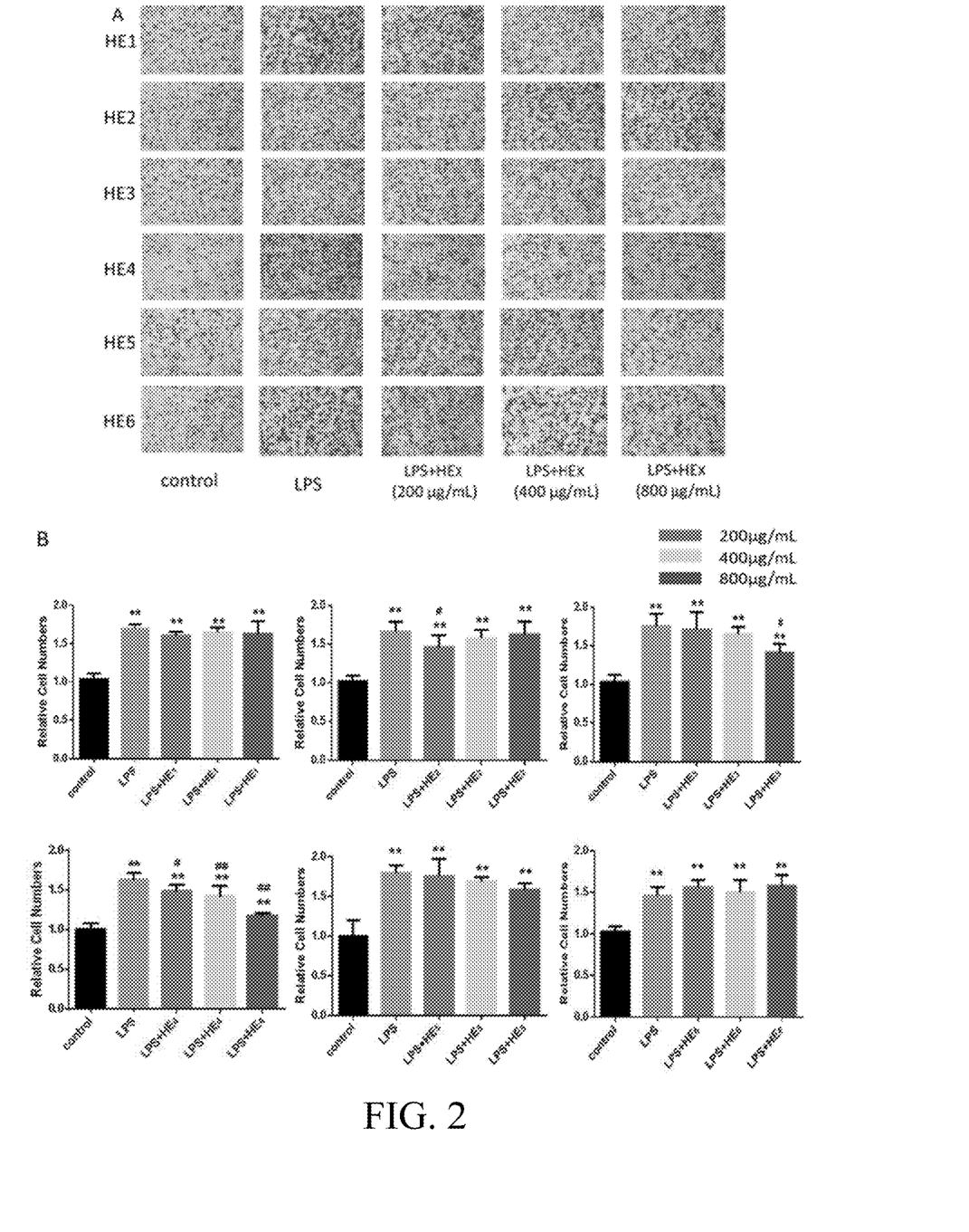

Transwell migration assay was used to detect the activity of HE1-HE6 in inhibiting the macrophage migration. The results are shown in FIG. 2. After induction with LPS, the macrophage migration activity is increased significantly. After adding the six eluted products, HE3 and HE4 can significantly inhibit the migration of macrophages RAW264.7 induced by LPS. Considering that the yield of HE3 eluate was low and it had migration inhibitory activity only at a high concentration, the next step was mainly to isolate and purify HE4.

Figure 3:
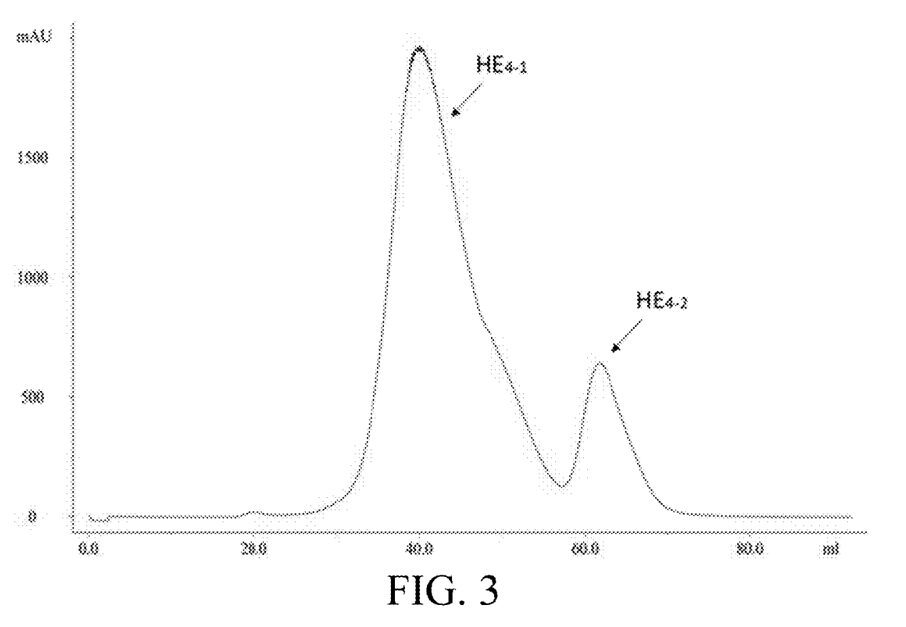
FIG. 3 shows an elution curve from Superdex30 gel filtration chromatography of HE4 in Example 1 of the present invention.

HE4 was separated by chromatography on a Superdex30 gel column. As shown in FIG. 3, HE4 is separated into two peaks. The products of each eluted peak were collected, and lyophilized after alcohol precipitation and desalting to obtain the products HE4-1 and HE4-2.

Figure 4:
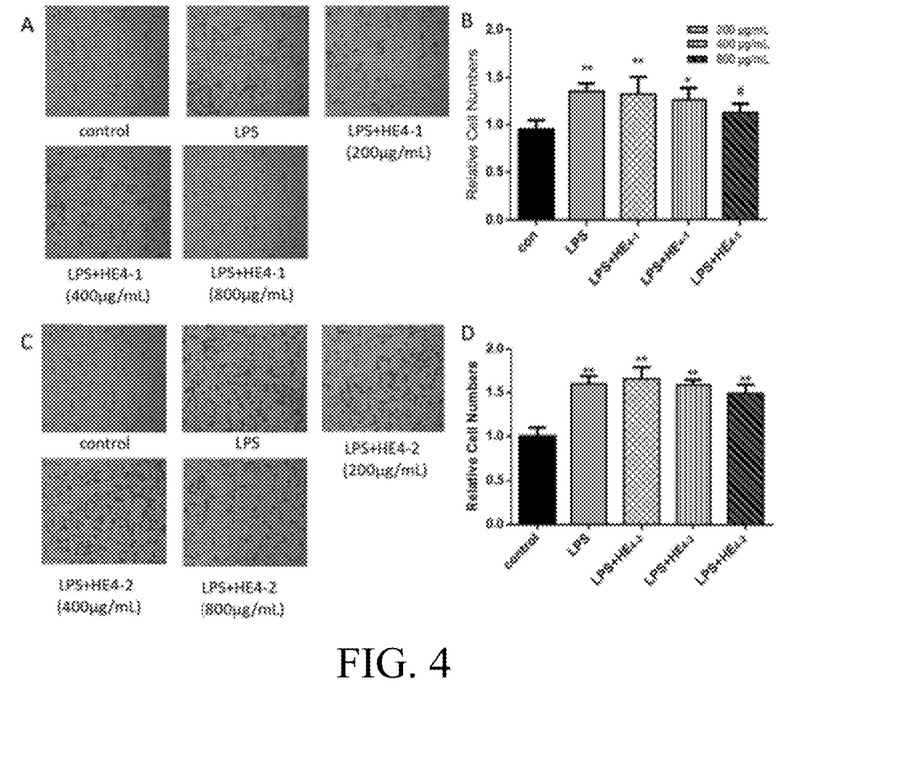
FIG. 4 shows the effect of RE1-HE6 on the survival rate of macrophages RAW264.7 in Example 1 of the present invention.

Transwell assay was used to detect the activity of HE4-1 and HE4-2 in inhibiting the migration of macrophages. The results are shown in FIG. 4. 800 μg/mL of HE4-1 can significantly inhibit the LPS-induced migration of macrophages RAW264.7, with an inhibition rate reaching 15.2%.

Figure 5:
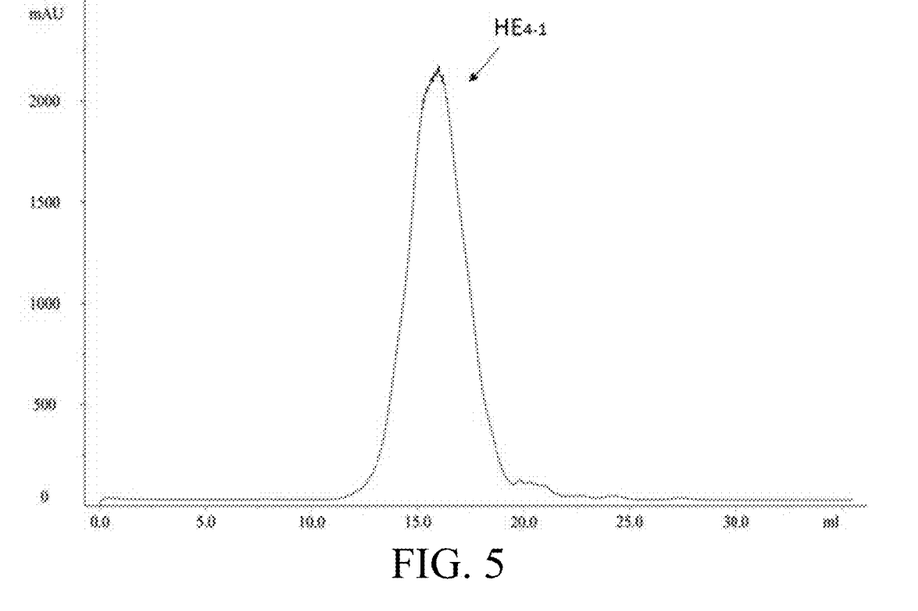
FIG. 5 shows an elution curve from Superdexpeptide gel filtration chromatography of HE4-1 in Example 1 of the present invention.
Figure 6:
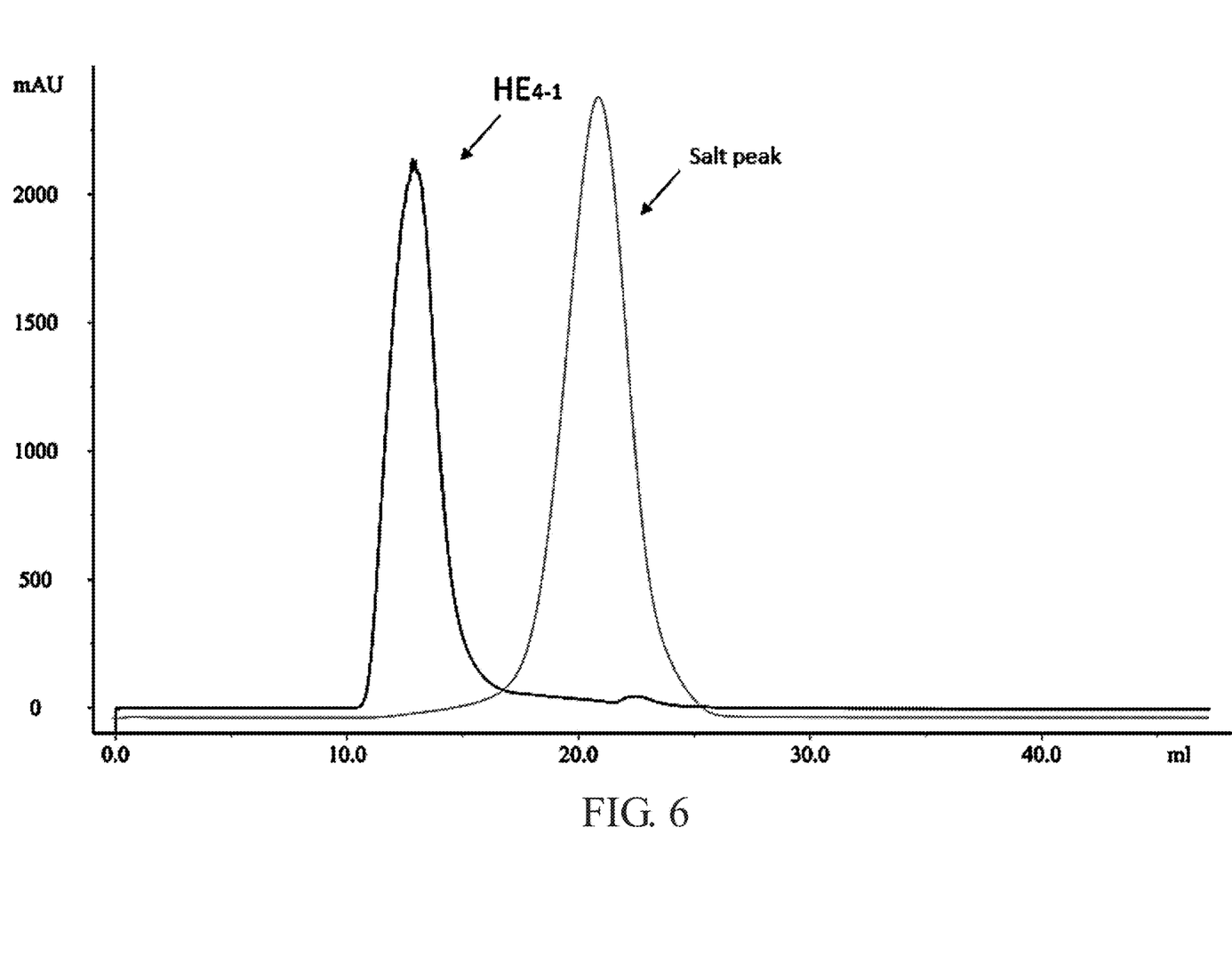
FIG. 6 shows an elution curve from G10 gel filtration chromatography of HE4-1 in Example 1 of the present invention.

HE4-1 was passed through Superdexpeptide gel filtration chromatography. The result is shown in FIG. 5. Only a single peak is eluted, namely HE4-1. Then HE4-1 was desalted by passing through a Sephadex G10 gel column (FIG. 6), and the HE4-1 peak before the salt peak was collected as the finally isolated and purified product.

Figure 7:
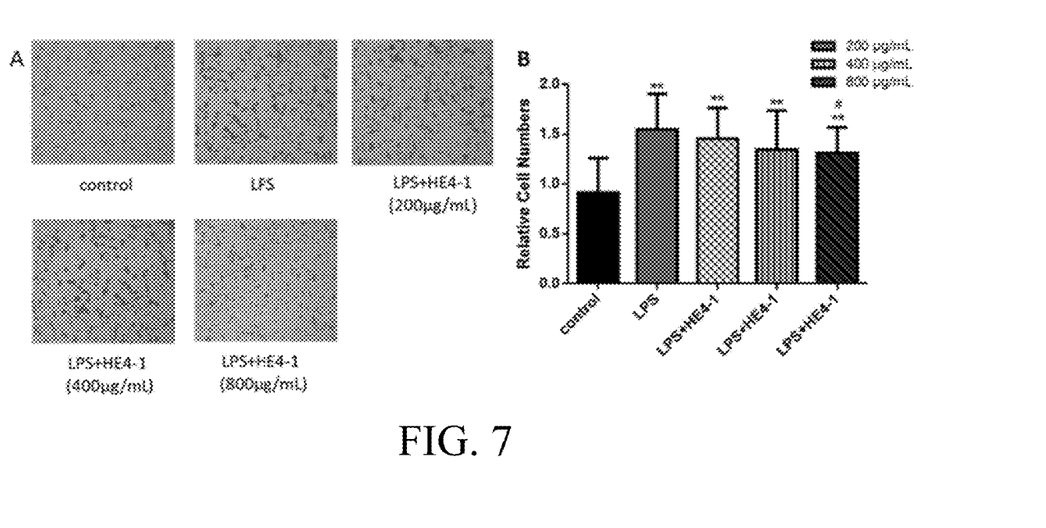

Transwell assay was used to test the activity of the finally eluted product HE4-1 to inhibit the migration of macrophages RAW264.7. The results are shown in FIG. 7. 1 μg/mL LPS can significantly promote the macrophage migration, while 800 μg/mL HE4-1 can inhibit the LPS-induced migration of macrophage RAW264.7 with an inhibition rate reaching 15.2%.

EXAMPLE 2

Sequencing of Leech Polypeptide

The leech polypeptide HE4-1 was shipped to Beijing Huada Protein Research And Development Center Co. Ltd for sequencing by LC-ESI-QUAD-TOF-MS/MS detection. Chromatographic column: Trap column: AcclaimPeP-map100 (75 μm×2 cm, 3 μm, 100A, Thermoscientific); analytical column: needle-type column manufactured by Beijing Huada Protein Research And Development Center Co. Ltd, packing material: VenusilxBPC, C18 (L), 5 μm, 150A (AgelaTechnologies). Chromatographic conditions: mobile phase A: 0.1% formic acid aqueous solution, mobile phase B: 0.1% formic acid in acetonitrile, gradient elution conditions: 0-48 min, A: 95%-20%, B: 5%-80%; 48-56 min, A: 20%-20%, B: 80%-80%; flow rate: 0.4 μL/min.

Figure 8:
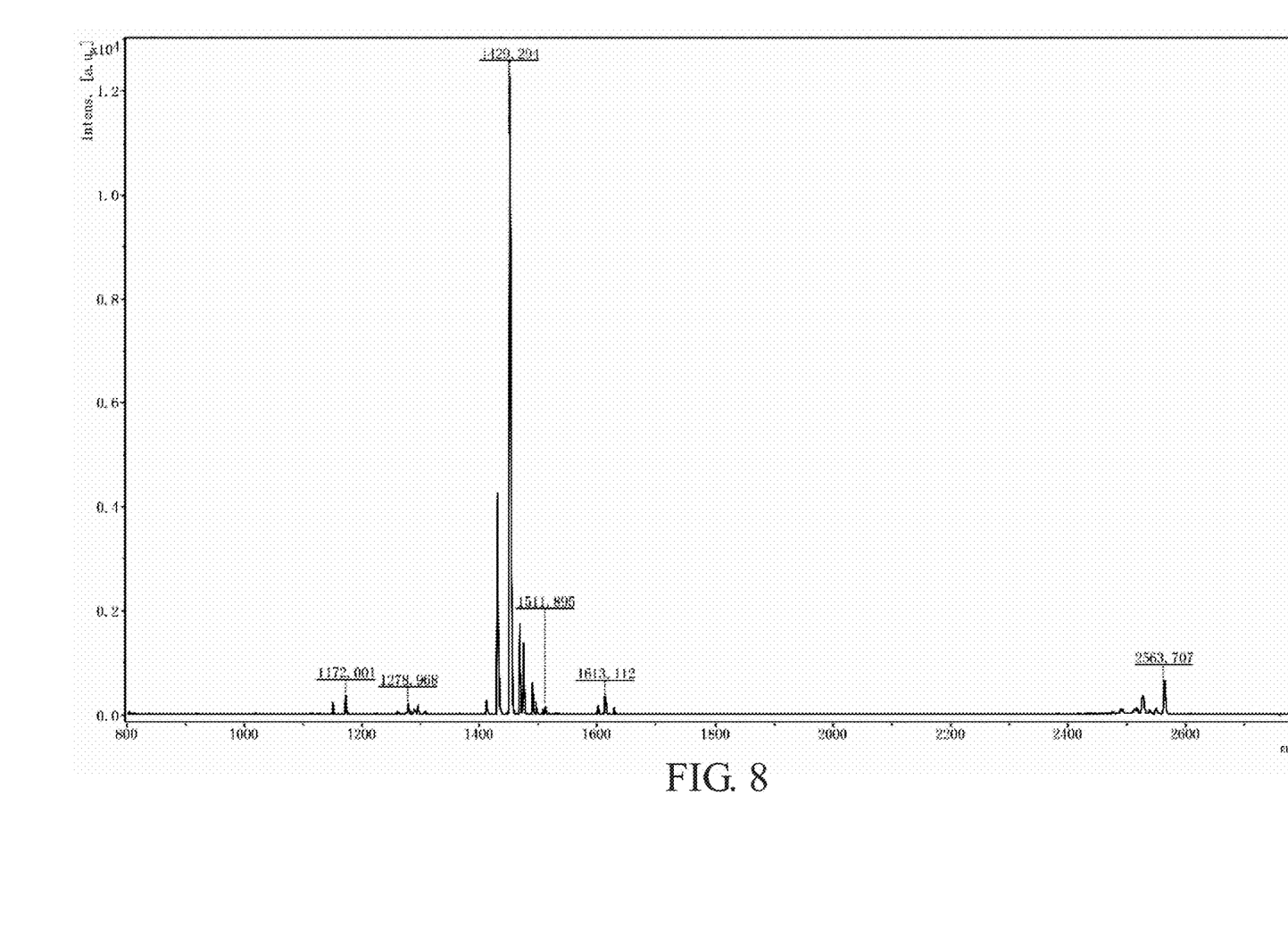
FIG. 8 is an MALDI-TOF mass spectrum of HE4-1 in Example 2 of the present invention.
Figure 9:
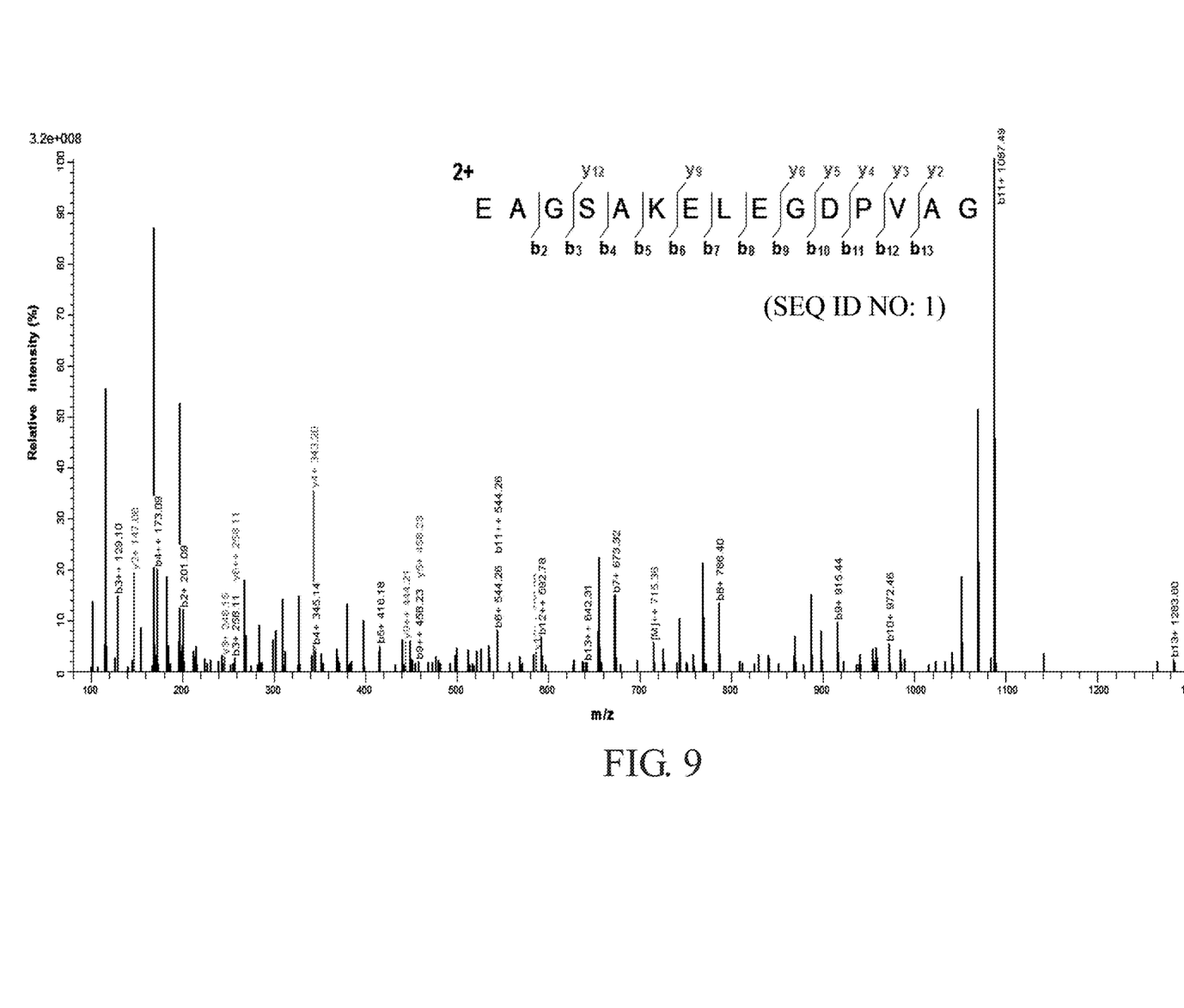
FIG. 9 is an LC-MS/MS mass spectrum of HE4-1 in Example 2 of the present invention.

As determined by high-resolution mass spectrometry, the molecular weight of leech polypeptide HE4-1 is 1429.294 Da (see FIG. 8) and the amino acid sequence is EAGSAKE-LEGDPVAG (SEQ ID: 1) (see FIG. 9).

EXAMPLE 3

Full Synthesis of Leech Polypeptide HE-D

The determined amino acid sequence_Glu-Ala-Gly-Ser-Ala-Lys-Glu-Leu-Glu-Gly-Asp-Pro-Val-Ala-Gly (SEQ ID NO: 1) was shipped to Sangon Bioengineering (Shanghai) Co., Ltd. for peptide synthesis. The synthesized peptide was designated as HE-D, which has a purity of 95% or more detected by HPLC. The structure was identified by ESI-MS.

EXAMPLE 4

Figure 10:
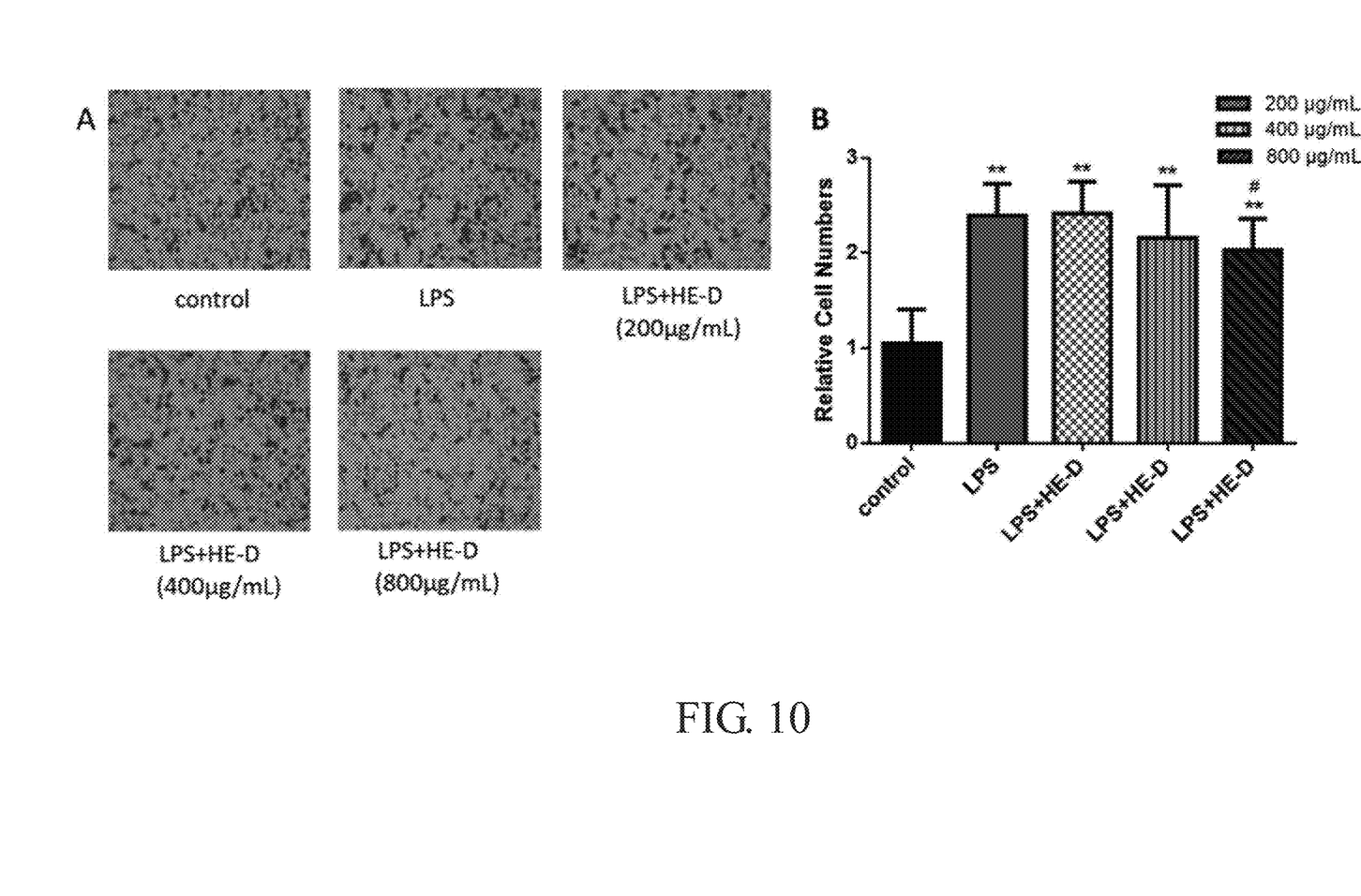

Activity of Synthetic Leech Polypeptide HE-D to Inhibit Macrophage Migration Transwell assay was used to detect the inhibition of HE-D on the migration activity of macrophages RAW264.7. The experiments were divided into five groups, including a blank control group, an LPS model group and 200, 400, 800 μg/mL HE-D groups. The results are shown in FIG. 10. 1 μg/mL LPS can significantly promote the macrophage migration, while 800 μg/mL HE-D can inhibit the LPS-induced migration of macrophage RAW264.7 with an inhibition rate reaching 14.9%.

EXAMPLE 5

Figure 11:
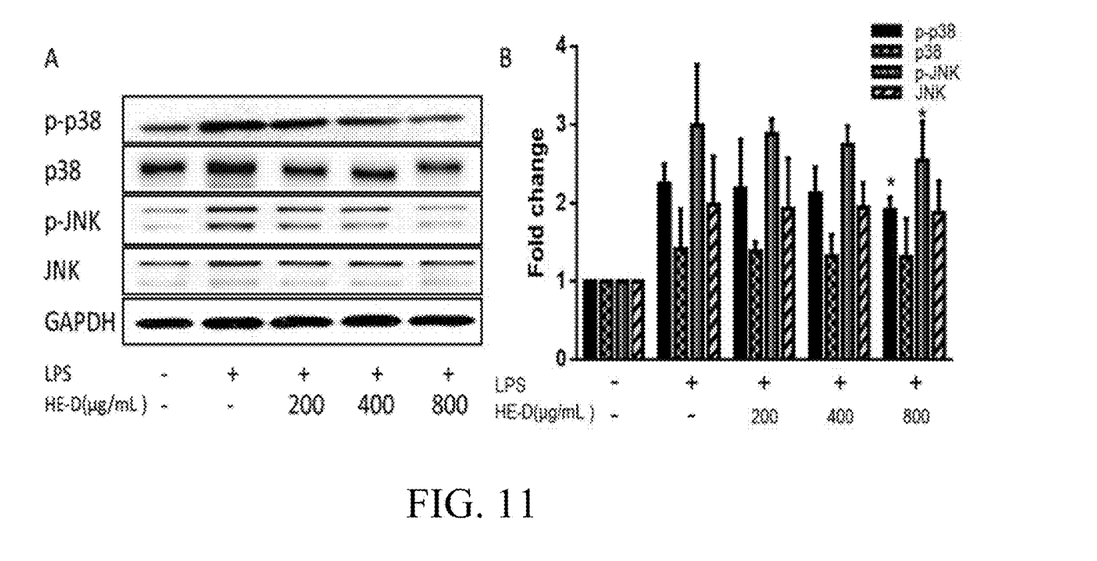

Study on Signal Pathways of Synthetic Leech Polypeptide HE-D Inhibiting Macrophage Migration The mechanism of HE-D inhibiting macrophages RAW264.7 was tested by Western-blot. The results are shown in FIG. 11. HE-D has no significant effect on the expression of JNK and total p38 protein, but 800 μg/mL HE-D can significantly inhibit the increase in expression levels of INK and phosphorylated p38 proteins induced by LPS, which indicates that HE-D can inhibit the migration of macrophages by regulating the levels of JNK and p38 phosphorylation.

EXAMPLE 6

Figure 12:
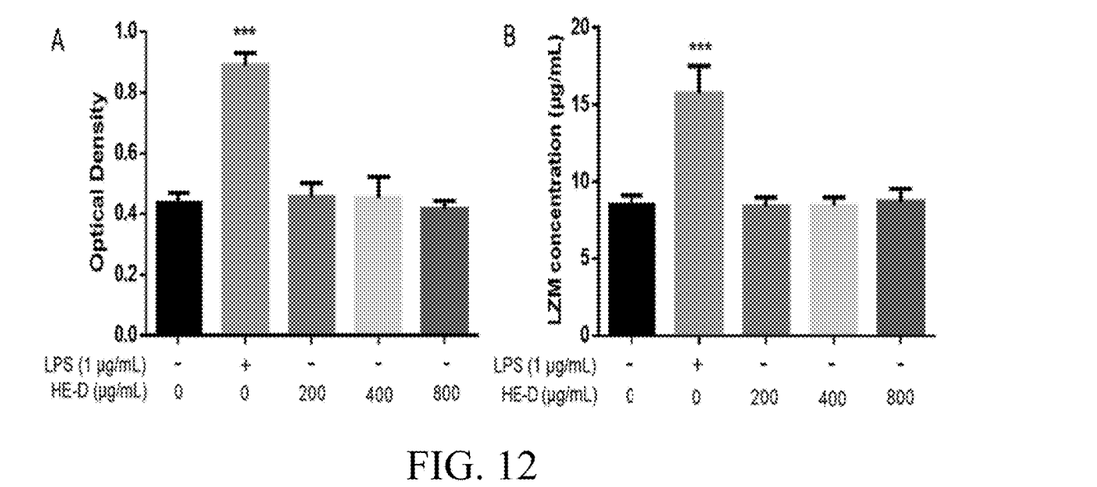

Effect of Synthetic Leech Polypeptide HE-D on Biological Functions of Macrophage The effects of HE-D on the phagocytosis ability and lysozyme activity of macrophage RAW264.7 were measured by neutral red phagocytosis test and lysozyme activity assay. The results are shown in FIG. 12. 1 μg/mL LPS can significantly increase the phagocytosis ability and lysozyme activity of macrophages, and 0-800 μg/mL HE-D has no obvious effect on the phagocytosis ability and lysozyme activity of macrophages RAW264.7.

Figure 13:
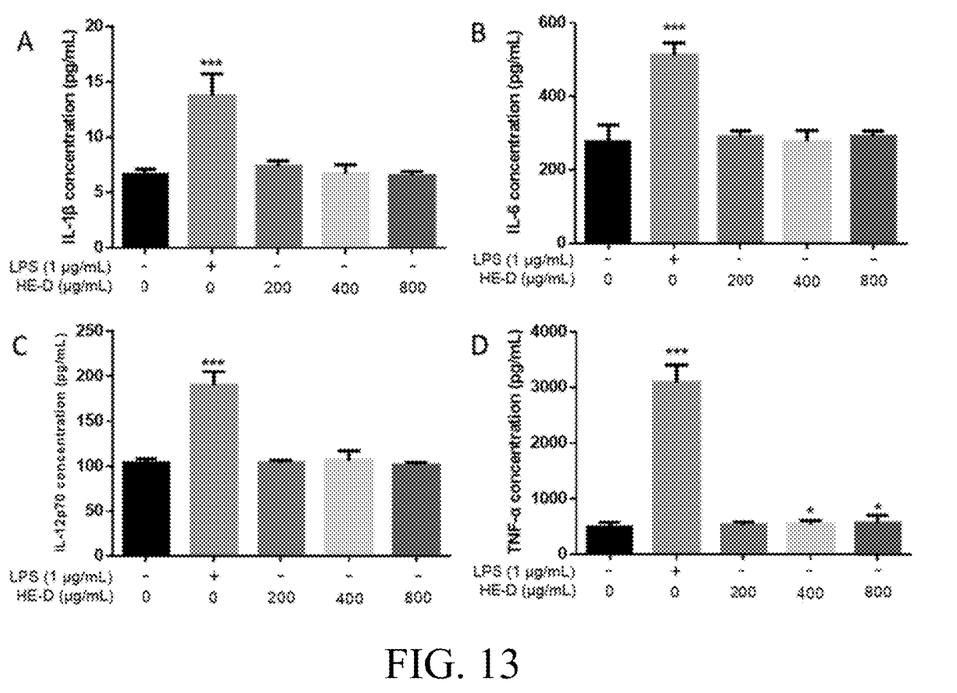

The effect of HE-D on the secretion of IL-1, IL-6, IL-12, and TNF-α by macrophages RAW264.7 was detected by ELISA. The results are shown in FIG. 13. 1 μg/mL LPS can significantly promote the release of the four inflammatory factors; and 0-800 μg/mL HE-D has no significant effect on the ability of macrophages to secrete the proinflammatory factors IL-1, IL-6, and IL-12, and 400 and 800 μg/mL HE-D can promote the secretion of TNF-α, but the promotion effect is small and is 11.4%.

In summary, the mechanism of HE-D inhibiting macrophages RAW264.7 was tested by Western-blot. The results in FIG. 11 show that HE-D has no significant effect on the expression of INK and total p38 protein, but 800 μg/mL HE-D can significantly inhibit the increase in expression levels of JNK and phosphorylated p38 proteins induced by LPS, which indicates that HE-D can inhibit the migration of macrophages by regulating the levels of JNK and p38 phosphorylation. HE-D has basically no effect on the biological functions of macrophages at the same time of inhibiting the migration of macrophages, which can effectively reduce the adverse reactions caused by HE-D. Therefore, synthetic leech polypeptide HE-D can be used for the early prevention of atherosclerosis and has the potential to prevent the further development of AS.

It should be finally noted that the foregoing descriptions are only preferred embodiments of the present invention, and are not intended to limit the present invention. Although the present invention is described in detail with reference to the foregoing embodiments, those of ordinary skill in the art should understand that they can still make modifications to the technical solutions described in the foregoing embodiments or make equivalent substitutions to some of the technical solutions. Any modification, equivalent replacement, or improvement made within the spirit and principle of the present invention shall fall within the protection scope of the present invention. The specific implementations of the present invention are described above, but are not intended to limit the protection scope of the present invention. Those skilled in the art should understand that various modifications or deformations may be made without creative efforts based on the technical solutions of the present invention, and such modifications or deformations shall fall within the protection scope of the present invention.

What is claimed is:

1. A leech polypeptide, having an amino acid sequence as shown in SEQ ID No: 1.

2. The leech polypeptide according to claim 1, wherein the polypeptide is produced by solid-phase polypeptide synthesis.

3. A method for preventing or treating a disease caused by macrophage migration, comprising:
   administering a leech polypeptide to a subject in need thereof, wherein the leech polypeptide has an amino acid sequence as shown in SEQ ID NO: 1.

4. The method according to claim 3, wherein the polypeptide is produced by solid-phase polypeptide synthesis.

5. The method according to claim 3, wherein the disease is atherosclerosis.

6. A method of preparing a drug by synthesizing the peptide of SEQ ID NO: 1 by solid-phase synthesis, and isolating the peptide and adding a pharmaceutically acceptable excipient.

* * * * *